United States Patent [19]

Herwig et al.

[11] 4,409,421
[45] Oct. 11, 1983

[54] PROCESS FOR THE PREPARATION OF PURE TERT.-OLEFINS

[75] Inventors: Jens Herwig; Bruno Schulwitz, both of Cologne; Bernhard Schleppinghoff; Hans-Volker Scheef, both of Dormagen; Peter M. Lange, Leverkusen, all of Fed. Rep. of Germany

[73] Assignees: EC Erdolchemie GmbH, Cologne; Bayer Aktiengesellschaft, Leverkusen, both of Fed. Rep. of Germany

[21] Appl. No.: 385,225

[22] Filed: Jun. 4, 1982

[30] Foreign Application Priority Data

Jun. 19, 1981 [DE] Fed. Rep. of Germany ....... 3124294

[51] Int. Cl.³ ........................... C07C 7/01; C07C 7/12
[52] U.S. Cl. .................................... 585/833; 585/327; 585/649; 585/809; 585/824; 585/840; 585/865; 585/324; 568/917; 568/697
[58] Field of Search ............... 585/324, 327, 648, 649, 585/809, 820, 824, 823, 864, 866, 830, 833, 834, 839; 568/917, 697

[56] References Cited

U.S. PATENT DOCUMENTS

| | | | |
|---|---|---|---|
| 3,170,000 | 2/1965 | Verdol | 585/839 |
| 3,409,691 | 11/1968 | Small | 585/824 |
| 3,489,808 | 4/1970 | Eberly, Jr. | 585/824 |
| 3,634,535 | 1/1972 | Haunschied | 585/824 |
| 3,751,507 | 8/1973 | Walker | 585/824 |
| 3,922,217 | 11/1975 | Cohen et al. | 585/824 |
| 4,287,379 | 9/1981 | Brunner et al. | 585/824 |
| 4,320,232 | 3/1982 | Volkamer et al. | 585/824 |

FOREIGN PATENT DOCUMENTS 22510  7/1979  European Pat. Off. ............ 585/824

*Primary Examiner*—Delbert E. Gantz
*Assistant Examiner*—A. Pal
*Attorney, Agent, or Firm*—Sprung, Horn, Kramer & Woods

[57] ABSTRACT

Pure tert.-olefins are prepared from mixtures of hydrocarbons, which contain at least one such tert.-olefin, by reaction with an alkanol to give the corresponding alkyl tert.-alkyl ethers, and subsequent cleavage of these ethers back to the corresponding pure tert.-olefins and the alkanol, and the separation of the pure tert.-olefin from the alkanol. For this, the alkanol present after the cleavage of the ether is separated from the tert.-olefin to the extent of 60 to 99% by weight by distillation, and the residual amount of alcohol in the olefin fraction is removed by adsorption from this fraction onto a synthetic ion exchanger as an absorber resin. The admixture of the alkanol to the mixture of hydrocarbons with at least one tert.-olefin is carried out partly by using the alkanol fraction arising from the separating off of the pure tert.-olefin, and partly by desorption of the alkanol from the absorber resin with the aid of the mixture of hydrocarbons containing at least 1 tert.-olefin.

7 Claims, No Drawings

PROCESS FOR THE PREPARATION OF PURE TERT.-OLEFINS

The present invention relates to a process for the preparation of pure tert.-olefins from gases containing at least 1 tert.-olefin by etherification with an alkanol and subsequent ether cleavage with the liberation of the pure tert.-olefins, the major amount of the alkanol being liberated in the ether cleavage being separated off by distillation from the tertiary olefin, and the residual amount of alkanol in the olefin fraction being removed by absorption on an absorber resin, and the alkanol to be employed in the etherification being partly taken from the bottom of the alkanol separation column and partly by desorption from the absorber resin loaded with alkanol.

Tertiary olefins are important precursors for the preparation of polymers and chemicals of higher value. The double bond on a tertiary carbon atom is an interesting structural feature which permits the production of numerous organic intermediates, such as, for example, pinacolin and neocarboxylic acids, or the production by dehydrogenation of conjugated diolefins, such as, for example, isoprene which can be further processed in the plastics, pharmaceuticals, plant protection and lubricant sectors. The prerequisite for these types of reactions is the availability of such tertiary olefins in as high a degree of purity as possible.

Since these tertiary olefins mainly arise in mixtures with other hydrocarbons in the spectrum of products from thermal and catalytic crackers, an isolation procedure must be applied for their purification. The isolation of the tertiary olefins from the hydrocarbon streams mentioned was hitherto primarily by the sulphuric acid process, in which the sulphuric acid esters of the tertiary alcohols corresponding to the tertiary olefins were initially formed, and are then converted back by splitting off the sulphuric acid to the tertiary olefin. This process is severely restricted by the corrosiveness of the sulphuric acid and by the necessity of working up the waste sulphuric acid. In recent times, processes have been developed which, starting with a selective etherification of the tertiary olefin with an alkanol, achieve the isolation of the pure tertiary olefin via the decomposition of these ethers (European Patent Application No. 0,003,305; U.S. Pat. No. 3,170,000; German Offenlegungsschrift No. 2,924,869). The separation of the products resulting from the ether cleavage into tert.-olefin and alkanol is generally carried out by means of distillation, in which the tert.-olefins arise as the top product and the alkanol goes into the bottom. However, due to azeotropic effects, the top product often still contains alcohol, which can be separated from the tertiary olefin by a water wash, if a pure tertiary olefin is to be obtained. In this case, an aqueous solution of the alkanol is obtained, which can be reprocessed by distillation. For such a separation, however, additional expenditure of energy is necessary for the distillation step. In addition, depending on the area of application of the olefin, drying on a molecular sieve for the removal of $H_2O$ may be necessary.

The preparation of alkyl tert.-alkyl ethers, which are to be cleaved to give the pure tert.-olefin and the corresponding alkanol, is also known. It can be performed by reaction of mixtures, which contain at least one tert.-olefin in addition to other olefins and paraffin hydrocarbons, with an alkanol in the presence of acid catalysts. Examples of acid catalysts used are inorganic acids, such as sulphuric acid, or organic acids, such as p-toluenesulphonic acid, or acid cation exchangers containing sulphonic acid groups, based on cross-linked vinyl-aromatic polymers (German Auslegeschrift No. 1,224,294). To bring about completion of the formation of ether and to remove the heat of reaction, a part of the reaction mixture of olefin and an alkanol can be returned directly to the inlet material for the preparation reactor (German Offenlegungsschrift No. 2,911,077). A higher conversion of olefin can also be achieved by using several reactors arranged in series.

A process has now been found for the preparation of pure tert.-olefins from mixtures of hydrocarbons containing at least one tert.-olefin by reaction with an alkanol to give the alkyl tert.-alkyl ethers, separating off the residual hydrocarbons, which are substantially free from the tert.-olefins, from the alkyl tert.-alkyl ethers, cleavage of the alkyl tert.-alkyl ethers back to the tert.-olefins and the alkanol and separation of the pure tert.-olefins from the alkanol, which is characterized in that the alkanol, after the cleavage of the alkyl tert.-alkyl ether, is separated off by distillation from the tertiary olefin to the extent of 60 to 99% by weight, and the residual amount of alkanol in the olefin fraction is removed by absorption from this fraction onto a synthetic ion exchanger with groups exchanging cations or anions, or a mixture of these, as the absorber resin, and the alkanol necessary for the reaction to give the alkyl tert.-alkyl ethers is at least partially introduced by desorption of the alkanol from the absorber resin with the aid of the mixtures of hydrocarbons containing at least one tert.-olefin.

An alkanol which may be mentioned for the process according to the invention is a primary or secondary alcohol with 1 to 4 C atoms, such as methanol, ethanol, propanol, i-propanol, butanol, i-butanol, preferably methanol or ethanol, particularly preferably methanol.

Tert.-olefins which may be mentioned which can be prepared in a pure form according to the invention, are olefins with a branch in the carbon chain at the olefinic double bond with 4 to 10, preferably 4 to 8, particularly preferably 4 to 6, C atoms, such as i-butene, tert.-pentene, tert.-hexane, tert.-octene or tert.-decene. In a very particularly preferred manner, i-butene and isoamylene may be mentioned.

The tert.-olefin to be prepared in the pure form is introduced into the process according to the invention in the form of a mixture of hydrocarbons, which contains at least one such tert.-olefin. Such material streams contain in addition to the minimum of one tert.-olefin further olefins or paraffin hydrocarbons and, if appropriate, additionally water, nitrogen, CO or $CO_2$. Examples of such material streams are: crude $C_4$-cut or a $C_4$-raffinate I (after butadiene extraction) from a thermal cracker or a FCC crude product stream from a fluid catalytic cracker (FCC) or a $C_4/C_5$-LCC stream from a catalytic cracker (LCC=light catalytic cracker). Obviously, the FCC crude product stream can have been previously divided into a $C_4$-FCC stream and a $C_5$-FCC stream. Equally suitable is a $C_5$ stream from a thermal cracker, for example, a distillation fore-run in the isolation of aromatics. Other suitable product streams are those from a n-butene skeletal isomerisation or ani-butane dehydrogenation, in which i-butene is present. Examples of suitable inlet streams for the reaction of higher tert.-olefins are distillate cuts of the particular carbon number fractions or, in a manner analogous to that sketched for i-butene, dehydrogenation or skeletal isomerization streams of hydrocarbons with the appropriate C numbers. In the case where hydrocarbon mixtures, which contain more than one tert.-olefin, are employed, mixtures of several alkyl tert.-alkyl ethers can be produced. In the subsequent ether cleavage, these can then provide mixtures of several tert.-olefins, which are then present in a pure form and thus can be separated into the individual components more easily. Obviously, for the case where mixtures of several alkyl tert.-alkyl ethers are produced, these ethers can also be separated into the pure products before cleavage, so that after cleavage of the pure ethers, the pure individual components of the tert.-olefins are also isolated.

An example of the ratio of the alkanol to the tert.-olefin (s) which may be mentioned is 0.8 to 5 mols of alkanol per mol of tert.-olefin or per mole of the molar sum of several different tert.-olefins. In the case of the etherification of i-butene, in particular with methanol, the preferred range of excess of the alkanol which may be mentioned is for example 1 to 4, preferably 1.1 to 3 mols of alkanol per mol of i-butene. In the case of higher tert.-olefins, for which the equilibrium point for conversion into the corresponding ether significantly deviates from 100% conversion, it can also be preferred to use less than the stoichiometric amount of the alkanol. In this case, an example of a ratio which may be mentioned is 0.8 to 2, particularly preferably 0.9 to 1.5 mols of alkanol per mol of higher tert.-olefin.

The etherification within the scope of the process according to the invention takes place on an acid etherification contact catalyst in a manner which is in itself known, for example in the presence of a strong mineral acid or its anhydride, such as sulphuric acid, phosphoric acid, sulphur trioxide, oleum or phosphorus pentoxide, or on a strong acid ion exchanger, such as a sulphonic acid-containing styrene-divinylbenzene polymer or a sulphonic acid-containing formaldehyde-phenol resin.

An example of the temperature which may be mentioned is the range from 25° to 90° C., preferably from 45° to 75° C. An example of the volumetric hourly space velocity in liters of hydrocarbon inlet stream per liter of acid contact catalyst per hour which may be mentioned is a value of 0.05 to 50, preferably from 0.2 to 15. The pressure for the etherification is chosen so that the materials taking part in the process are present in liquid form. The range of pressure which may be mentioned is generally the range from 0.2 to 30 bars, preferably from 2 to 20 bars. The pressure in the lower range from 0.2 bar is only suitable for those tert.-olefins and the mixtures of hydrocarbons in which these tert.-olefins are contained, as well as for the alkanols used for the etherification, which are still liquid under these conditions of pressure.

The etherification step is then followed by a separation of the alkyl tert.-alkyl ether formed from the residual non-etherified hydrocarbon mixture with the olefins which cannot form ethers and the paraffin hydrocarbons as well as any residual tert.-olefin which did not react because of the position of the etherification equilibrium.

If appropriate, the ether can be precision-distilled from higher hydrocarbons and higher ethers in a subsequent distillation.

The subsequent cleavage of the alkyl tert.-alkyl ether or, in the case where several tert.-olefins are to be simultaneously reacted, of the mixture of such alkyl tert.-alkyl ethers, can be performed on catalysts with acid centers, for example on crystalline silica gel (as described in German Offenlegunsschrift No. 2,924,869) or on acid molecular sieves, which are optionally activated with hydrogen, in the range from about 190° to 350° C., preferably from 100° to 300° C.

Zeolites, acidic aluminum oxides and H-mordenites may be mentioned as examples of molecular sieves which can be used in the process according to the invention. Zeolites are understood here to mean water-containing silicate frameworks of the general formula $x[(M',M''_{0.5}) AlO_2].y SiO_2.zH_2O$ with $M'$=Li, Na, K etc. and $M''$=Mg, Ca, Sr, Ba, etc. (Fortschr. Mineral 42, 50 (1965)). They usually have a crystalline structure, as determined by X-ray diffraction analysis, and are porous. The pores are usually uniform in size, especially diameter. Furthermore, H-mordenites are understood to mean orthorhombic silicate frameworks of the formula $Na_8[(AlO_2)_8.(SiO_2)_{40}]. 24H_2O$, the Na atoms of which can be successively exchanged for H atoms (Am. Mineral, 39, 819 (1954)).

H-Mordenites are preferably employed. These molecular sieves which can be used according to the invention are available in their acidic $H^+$ form.

The acidic molecular sieves described can be employed according to the invention individually as well as in a mixture of 2 or more of the molecular sieves mentioned. In the case that the selectivity of the molecular sieve employed according to the invention as catalyst, or of the mixture of several molecular sieves, is to be increased, which, in general, is accompanied by a decrease in the activity and/or a decrease in the throughput, it can be of advantage to mix the molecular sieves used with, for example, 0.01 to 80% by weight, relative to the amount of the molecular sieves, of aluminum oxide and/or amorphous alumosilicates, and to employ the mixture thereby obtained as catalyst.

Such acid molecular sieves have, for example, an effective pore volume of, for example, 0.05 to 0.6 ml/g and an effective pore diameter of, for example, 3 to 15 Å. Their specific surface area is about 100 to 700 m²/g. This last-mentioned process can be performed at a temperature of about 100° to 300° C. in the gas phase or in the liquid phase under a pressure of about 0.1 to 50 bars. The loading of the contact catalyst is selected in the range from WHSV=0.5 to 5 g of substrate/g of catalyst/hour (WHSV=weight, hourly space velocity).

Activation with hydrogen can, for example, be carried out with 50 to 500 l of hydrogen per l of catalyst at about 100° to 450° C. and 1 to 50 bars for about 1 to 60 hours. In this ether cleavage, a mixture of the alkanol on which the ether is based and the tert.-olefin is then obtained.

The complete process for the preparation of pure tert.-olefins in the manner described can be reproduced by the following equation:

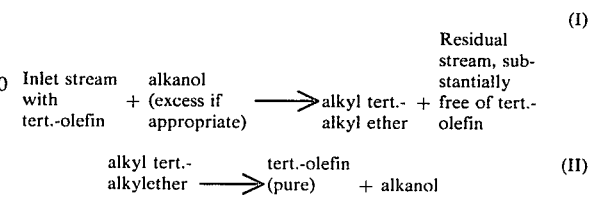

According to the invention, the amounts of alkanol produced after the cleavage of the alkyl tert.-alkyl ether are largely separated off by distillation (approx. 60–99% by weight) and to a lesser extent (1-40% by weight) are recovered from the olefin fraction by absorption of this alkanol onto an absorber resin. Furthermore, in accordance with the invention, this alkanol absorbed on the absorber resin is employed for the formation of the alkyl tert.-alkyl ether such that the inlet hydrocarbon stream with at least one tert.-olefin is led through the absorber resin loaded with the alkanol to bring about the desorption of this alkanol. In addition, the alkanol separated off by distillation is added to this stream and, if necessary, supplemented by fresh alkanol and led into the etherification reactor.

The formulations of the process represented above can thus be represented for the procedure according to the invention as follows:

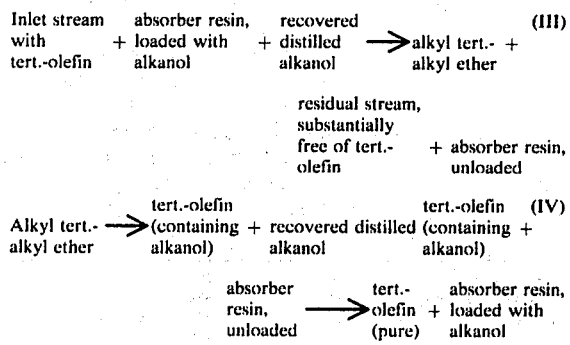

It is clear from the presentation similar to formulae, that all the alkanol employed for etherification is completely retrieved in the form of recovered distilled alkanol and in the form of alkanol recovered by the ether cleavage. Apart from the leakages unavoidable in an industrial process, and from small residual amounts of alkanol which are present either in the pure tert.-olefin or in the residual stream substantially freed of tert.-olefin, no addition of alkanol to the process according to the invention is thus necessary. On the contrary, the amount of alkanol once introduced within the scope of the conditions of the process described with replenishment of the slight leakage and other losses mentioned, is continuously circulated. The amount of alkanol circulated which may be mentioned is 0.8 to 5 mols per mol of tert.-olefin or per mol of the molar sum of several different tert.-olefins. If it is further assumed that the total amount of alkyl tert.-alkyl ether formed is consumed again in the ether cleavage, the total process according to the invention for the preparation of pure tert.-olefins can be summarised and represented by the following formulation:

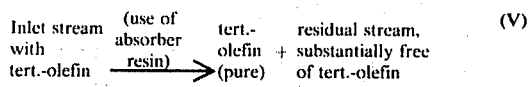

To carry out the process according to the invention, the absorber resin employed for absorption and desorption is divided into at least 2 layers, of which at least one is employed in a substantially alkanol-free state for the absorption of the alkanol arising from the ether cleavage, whilst another layer of absorber, already loaded with the alkanol, is put in the stream of the inlet materials for the process according to the invention for the desorption of the alkanol. It is occasionally necessary to put in another layer of absorber resin after the formation of the ether for the absorption of the excess alkanol from the residual stream freed of tert.-olefin, which is then put back in the inlet stream for desorption in order to re-introduce this collected alkanol. The layers of absorber resin provided for absorption and desorption are combined by a simple switching arrangement familiar to the specialist, such that this absorber layer is switched over to desorption in good time before the "discharge" of the alkanol through the absorber layer, and a layer of absorber resin, which has become in the meantime substantially free of alkanol by desorption, is now available again for alkanol absorption. This switching-over of the different layers of absorber resin from absorption to desorption can be performed rapidly by simultaneous actuation of all the necessary shut-off systems so that the process according to the invention can be performed completely continuously. Obviously, more than one layer of absorber can also be employed for alkanol absorption, and in this case, a second absorber layer is put in after the first as a back-up layer. By this means, the capacity for alkanol in the first layer of absorber can be completely exploited, since a partial "break-through" of the alkanol through the first layer into the second layer can be held back. The "break-through" can be recognised in a simple manner, for example by gas-chromatographic measurement or by infrared detectors in the exit stream of hydrocarbons.

The absorption of the excess alkanol can be carried out, for example, in the range from 0° to 60° C., preferably 15° to 35° C. The selected pressure can, for example, be 0.2 to 20 bars. The material streams to be freed of alkanol are in a liquid state for absorption. The lower portion of the range of pressure given is only suitable when higher tert.-olefins and/or higher alkanols are reacted, which are still in a liquid state together with the alkyl tert.-alkyl ethers formed from them, even under a reduced pressure.

In principle, the desorption of the alkanol with the aid of the inlet stream can take place under the same conditions as the absorption. In general, it is desirable to maintain the desorption time about as long as the absorption time, in order, on the one hand, to have a regenerated layer available on saturation of the resin employed for absorption, and on the other hand, to deliver the alkanol as uniformly as possible into the etherification reaction. For this, the desorption can also be performed in a somewhat higher range of temperature, for example 20° to 100° C., preferably 30° to 60° C., and under a pressure of, for example, 3 to 30 bars, preferably 5 to 15 bars. The entire range for the desorption is thus 0.2 to 30 bars at 0°-100° C. Surprisingly, it has been observed that a more rapid desorption can be achieved, with the aid of the inlet stream, the higher the content of tert.-olefins in it. This permits a method of running, in which the desorption temperature can be kept low, for example in the vicinity of the absorption temperature. This results in a method of running which is extremely energy-saving, and is superior, in respect of energy, to the processes known hitherto for the separation of methanol, that is to say a water wash with subsequent working-up by distillation of the alkanol/water mixture.

Examples of absorber resins for the process according to the invention which may be mentioned are synthetic ion exchangers with groups exchanging cations or anions. Such ion exchangers have, for example, a matrix based on cross-linked styrene polymers. Examples of cross-linking agents which may be mentioned are divinylbenzene, trivinylbenzene or trivinylcyclohexane in an amount of about 0.3–80% by weight, preferably 1–65% by weight, particularly preferably 2–50% by weight, relative to the total amount of the comonomers. The matrix can, however, also be a phenol/formaldehyde condensate, a (meth)acrylic resin or an epichlorohydrin/polyamine condensate, in each case in cross-linked form. Such cross-linked matrices can be employed in the form of gels or in macroporous form.

Examples of exchanging groups on these matrices which may be mentioned are: sulphonic acid groups, phosphoric acid groups and carboxyl groups, in each case in the $H^+$ form or, for example, in the $Na^+$, $K^+$, $NH_4^+$ or $Ca^{++}$ form. Other possible examples of exchanging groups are: $—NR_3^+$, such as $—N(CH_3)_3^+$ or $—N(CH_3)_2CH_2CH_2OH^+$, or $NR_2$, such as $N(CH_3)_2$, as well as N-oxide groups. These groups containing N can have as an exchangeable counter-ion, for example, the OH, Cl, or $SO_4$ ion. Anion exchangers of this type with the group $—N(CH_3)_3^+$ are known to the specialist as type I, and those with the group $—N(CH_3)_2CH_2C-H_2OH^+$ are known as type II.

Ion exchangers of the type described have, for example, total capacities for the exchange of ions of about 0.5–6 equivalent/1 of resin. These resins and the processes for their preparation have been known for a long time (Hefferich, Ion Exchange, McGraw-Hill, New York 1962).

Examples of resins which can be used according to the invention are: gel-like styrene/divinylbenzene resins containing sulphonic acid groups, macroporous styrene/divinylbenzene resins containing sulphonic acid groups, gel-like or macroporous (meth)acrylic acid/divinylbenzene resins containing carboxyl groups, gel-like or macroporous styrene/divinylbenzene anion exchangers of type I or II, macroporous or gel-like styrene/divinylbenzene resins with $—N(CH_3)_2$ groups, weakly basic macroporous resins of the acrylamide/divinylbenzene type, strongly basic macroporous resins of the acrylamide/divinylbenzene type or cross-linked phenol/formaldehyde resins containing sulphonic acid groups. This list is not complete and is not restricted to the resins mentioned. Many of these resins are commercial products of various manufacturers.

The loading of the absorber layer for absorption and desorption is selected within the range of hourly space velocity WHSV (weight hourly space velocity) of 0.1 to 100, preferably 0.5 to 20, particularly preferably from 1 to 15 kg of inlet stream per kg of absorber per hour.

In the etherification step, separating off the non-reacted alkanol is not absolutely necessary, since cleavage of the alkyl tert.-alkyl ether produces the same alkanol. Amounts of alkanol which are present in the residual stream largely freed of tert.-olefin can, if necessary, also be removed by absorption and re-introduced.

It is obvious that valuable materials which remain after incomplete reactions, if appropriate after isolation, can be re-introduced into the individual steps of the process according to the invention. For example, incompletely reacted tert.-olefin in the residual stream, particularly in the case of tert.-olefins with higher C numbers, can be separated off, for example by distillation, and can, together with the inlet stream, be re-introduced into the etherification step. Furthermore, if necessary, incompletely cleaved ether can be collected during isolation of the pure tert.-olefin and the separating-off of the alkanol which has been cleaved off, and re-introduced into the ether cleavage. It is equally obvious that unavoidable impurities, such as undesired decomposition products or oligomerisation products, are to be eliminated by outward transfer of small part-streams from the part-streams arising in the process, and to keep their concentrations in all part-streams as low as possible. Small amounts of alkanol, which have been transferred out and whose recovery is not economically viable, are replaced by the addition of fresh alkanol, as already mentioned.

EXAMPLE

A thermostatic continuous flow reactor with an internal diameter of 20 mm is employed for the etherification of a partially hydrogenated $C_5$ hydrocarbon stream from a thermal cracker (aromatics fore-run) with methanol. The temperature is checked using temperature measuring points which are arranged 100 mm apart. 100 g/h of the said hydrocarbon stream with 20% by weight of i-amylene are etherified in this reactor and 8.6 g/h of methanol on 110 g of a strongly acid macroporous cation exchanger doped with 0.75 g/l of elemental palladium, known from German Offenlegungsschrift No. 3,036,481, at 70° C. and 10 bars. Investigation by gas chromatography of the product stream indicated the following composition

| | |
|---|---|
| i-amylenes | 4.1% by weight |
| TAME (tert.-amyl methyl ether) | 20.9% by weight |
| methanol | 1.2% by weight |
| residual $C_5$ hydrocarbons | 72.1% by weight |
| higher ethers and hydrocarbons | 1.7% by weight |
| Conversion of i-amylene: | 78% by weight of the i-amylene employed. |

This product stream is collected in an intermediate tank and transferred from there to a still. In this distillation, the top product taken is the $C_5$ hydrocarbon stream with the residual amounts of i-amylene and methanol, the bottom product taken is TAME in a mixture with higher ethers. This bottom product is worked up in a further distillation column to pure TAME (as the top product with 99.9% by weight of TAME). Higher ethers, as the bottom product of this purification distillation, are transferred out as undesired products.

The purified TAME is run into a cleavage reactor, in which the TAME is cleaved back into i-amylene and methanol.

The cleavage reactor is a thermostatic continuous flow reactor with an internal diameter of 25 mm, equipped with temperature measuring points (100 mm apart) and an adjustable pressure controller. The metering-in of the TAME is by means of a diaphragm-piston pump.

The reaction conditions are:

| | |
|---|---|
| catalyst | 100 g of $H^+$—mordenite |
| feed | 100 g of TAME/hour (99.9% by weight purity) |
| WHSV | 1 g of substrate/g of contact.hour |
| pressure | 10 bars |
| temperature | 140° C. |
| conversion of TAME | 96% |

Gas chromatographic analysis of the cleavage product gives the following composition:

| | |
|---|---|
| TAME | 3.8% by weight |
| 2-methylbut-2-ene | 49.2% by weight |
| 2-methylbut-1-ene | 16.8% by weight |

| | |
|---|---|
| 3-methylbut-1-ene | — |
| methanol | 28.0% by weight |
| dimethyl ether | 1.6% by weight |
| H$_2$O | 0.6% by weight |

This cleavage product is stored in an intermediate tank cooled to about 0° C., and is separated into the desired methylbutenes and the residual TAME and methanol in a downstream distillation step. In this distillation, the top product obtained is:

| | |
|---|---|
| 3-methylbut-1-ene | <0.1% by weight |
| 2-methylbut-2-ene | 71.1% by weight |
| 2-methylbut-1-ene | 24.3% by weight |
| methanol | 4.6% by weight |
| TAME | <0.1% by weight |

The composition of this top product corresponds to the azeotrope of i-amylene and methanol. The methanol content in the bottom from this distillation is more than 82% by weight.

To remove the methanol and to prepare the pure i-amylenes, the top product is run over an absorber. This absorber consists of two steel reactors with an internal diameter of 25 mm and a total volume of 250 ml, operated in alternation. The reactors are jacket-heated and fitted with temperature-measuring points. The reactor pressure is maintained by a pressure controller. The feed stream is metered in upwards by means of a diaphragm-piston pump. At the outlet of the reactor, instantaneous and average samples are taken and investigated by gas chromatography. The reactors operated in alternation are each charged with 120 ml of a macroporous styrene/divinylbenzene anion exchanger with dimethylbenzylamino groups (commercial product Lewatit MP 62 from Bayer AG). For the absorption of methanol, 400 g/hour of the top product of the distillation described are passed upwards through one of the two absorbers. The pressure is maintained at 1 bar and the temperature at 20° C. The absorption effects and their change with time are given in the following table:

| Product throughput | CH$_3$OH concentration at the absorber outlet |
|---|---|
| 400 g | 0.1% by weight |
| 800 g | 0.1% by weight |
| 1,200 g | 0.1% by weight |
| 1,600 g | 0.2% by weight |

Subsequently the product stream is switched over to the second absorption reactor, which is operated in the same manner. For desorption of the methanol, the loaded absorber is flushed with the aromatic fore-run which is to be etherified. The reaction conditions for this are: P=5 bars; T=35° C.; throughput=440 g/hour.

The methanol concentration in the eluate and its change over 3 hours are listed in the following table:

| Product throughput | CH$_3$OH concentration |
|---|---|
| 400 g | 8.6% by weight |
| 880 g | 2.3% by weight |
| 1,332 g | 0.1% by weight |

The absorption reactor is cooled down to 20° C. and the reactor pressure is decreased to 1 bar. In this form the absorber is ready for operation in the next switch-over to methanol absorption.

What is claimed is:

1. In a process for the preparation of a pure tertiary olefin comprising the steps of:
    (A) contacting at least one tertiary olefin in a hydrocarbon stream within which it is in admixture with other hydrocarbons with an alkanol whereby to form an alkyl tertiary alkyl ether;
    (B) separating off the residual hydrocarbons which are largely free of tertiary olefins from said alkyl tertiary alkyl ether;
    (C) cleaving said alkyl tertiary alkyl ether back to said tertiary olefin and alkanol; and
    (D) separating pure tertiary olefin from alkanol,
  the improvement wherein:
    (E) said alkanol, at the cleavage from said tertiary alkyl ether, is separated off by distilling off from said tertiary olefin to the extent of 60 to 99% by weight;
    (F) residual alkanol in admixture with said tertiary olefin is separated from said tertiary olefin by passing the mixture of residual alkanol and tertiary olefin over a synthetic ion exchanger which contains groups which exchange cations or anions or a mixture thereof whereby said alkanol becomes absorbed on said synthetic ion exchanger and substantially pure tertiary olefin is removed; and thereafter absorbed alkanol on said synthetic ion exchanger is desorbed by contacting said synthetic ion exchanger containing absorbed alkanol with a mixture of hydrocarbons containing at least one tertiary olefin; and
    (G) reacting said desorbed alkanol from step (F), while in admixture with at least one tertiary olefin to form said alkyl tertiary alkyl ether.

2. A process according to claim 1, wherein said synthetic ion exchanger is an ion exchanger with the matrix composed of styrene/divinylbenzene, phenol/formaldehyde, (meth)acrylic acid (derivative)/divinylbenzene or epichlorohydrin/polyamine.

3. A process according to claim 1, wherein 0.8 to 5 mols of alkanol are reacted according to step (A) per mol of tertiary olefin or mixture of tertiary olefins, said alcohol comprising at least in part some of the alkanol desorbed by desorption with said mixture of hydrocarbons and alkanol removed from a mixture of alkanol and tertiary olefin by distillation.

4. A process according to claim 1, wherein said alkanol is absorbed at 0°–60° C. under a pressure of 0.2 to 20 bars.

5. A process according to claim 1, wherein alkanol desorption is carried out at a temperature of 0° to 100° C. at a pressure of 0.2 to 30 bars.

6. A process according to claim 4, wherein alkanol desorption is carried out at a temperature of 0° to 100° C. under a pressure of 0.2 to 30 bars.

7. A process according to claim 1, wherein the loading of the absorber layer is 0.1 to 100 kilograms of inlet stream per kilogram of absorber per hour.

* * * * *

UNITED STATES PATENT AND TRADEMARK OFFICE
CERTIFICATE OF CORRECTION

PATENT NO. : 4,409,421
DATED : October 11, 1983
INVENTOR(S) : JENS HERWIG et al

It is certified that error appears in the above-identified patent and that said Letters Patent is hereby corrected as shown below:

| | |
|---|---|
| Under "Assignees" | Delete "Erdolchemie" and insert -- Erdölchemie -- |
| Under "U.S. Patent Documents" | Third line delete "4/1970" and insert -- 1/1970 -- |
| Under "U.S. Patent Documents" | Fourth line delete "Haunschied" and insert -- Haunschild -- |
| Abstract, line 11 | Delete "adsorption" and insert -- absorption -- |
| Column 10, line 25 | End of line delete "from" |

Signed and Sealed this

Fifteenth Day of May 1984

[SEAL]

Attest:

Attesting Officer

GERALD J. MOSSINGHOFF

Commissioner of Patents and Trademarks